(12) United States Patent
Koch

(10) Patent No.: US 8,883,197 B2
(45) Date of Patent: Nov. 11, 2014

(54) TRANSDERMAL, THERAPEUTIC SYSTEM WITH ACTIVATABLE OVERSATURATION AND CONTROLLED PERMEATION PROMOTION

(75) Inventor: Andreas Koch, Melsbach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1811 days.

(21) Appl. No.: 11/793,983

(22) PCT Filed: Dec. 8, 2005

(86) PCT No.: PCT/EP2005/013133
§ 371 (c)(1),
(2), (4) Date: Jun. 25, 2007

(87) PCT Pub. No.: WO2006/072329
PCT Pub. Date: Jul. 13, 2006

(65) Prior Publication Data
US 2008/0113013 A1   May 15, 2008

(30) Foreign Application Priority Data

Dec. 24, 2004  (DE) .......................... 10 2004 062 614

(51) Int. Cl.
| | |
|---|---|
| *A61K 9/70* | (2006.01) |
| *A61K 47/10* | (2006.01) |
| *A61K 47/12* | (2006.01) |
| *A61K 47/22* | (2006.01) |

(52) U.S. Cl.
CPC .............. *A61K 9/7092* (2013.01); *A61K 9/7053* (2013.01); *A61K 47/10* (2013.01); *A61K 47/12* (2013.01); *A61K 47/22* (2013.01)
USPC ........................................................ 424/449

(58) Field of Classification Search
None
See application file for complete search history.

(56) References Cited

U.S. PATENT DOCUMENTS

| | | | |
|---|---|---|---|
| 4,031,894 A | 6/1977 | Urquhart et al. | |
| 4,698,062 A | 10/1987 | Gale et al. | |
| 4,788,064 A * | 11/1988 | Patel et al. | 424/449 |
| 4,917,676 A | 4/1990 | Heiber et al. | |
| 5,128,137 A | 7/1992 | Muller et al. | |
| 6,019,988 A | 2/2000 | Parab et al. | |
| 7,056,528 B1 * | 6/2006 | Bracht | 424/449 |
| 2003/0082227 A1 | 5/2003 | Sournac et al. | |

FOREIGN PATENT DOCUMENTS

| | | |
|---|---|---|
| EP | 0273004 | 6/1988 |
| EP | 0384266 | 8/1990 |
| EP | 0857488 | 8/1998 |
| JP | A-S64-85912 | 3/1989 |
| JP | A-H02-264715 | 8/1992 |
| WO | WO 01/19352 | 3/2001 |

OTHER PUBLICATIONS

English Machine Translation of EP 0384266.*

* cited by examiner

*Primary Examiner* — Rachael E Bredefeld
(74) *Attorney, Agent, or Firm* — D. Peter Hochberg; Sean F. Mellino; Richard A. Wolf

(57) ABSTRACT

A transdermal therapeutic system (TTS) that is essentially composed of two compartments and is provided with activatable oversaturation and controlled permeation promotion. The invention more particularly relates to a TTS wherein an oversaturated active ingredient solution is produced in an active-substance-containing polymer matrix when the system is applied to the skin, caused by the controlled supply of one or several substances promoting the permeation of the pharmaceutical active ingredient; to the two compartments from which the inventive transdermal therapeutic system is assembled; and to the production of the transdermal therapeutic system from the two compartments.

34 Claims, 5 Drawing Sheets

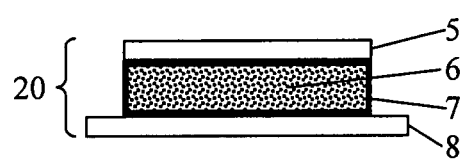
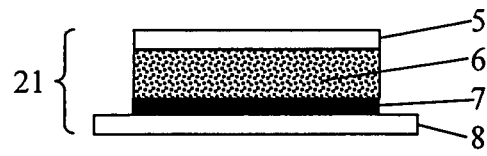
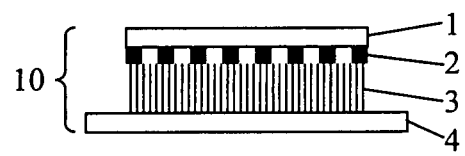
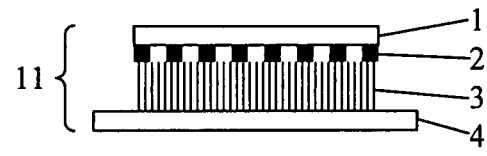
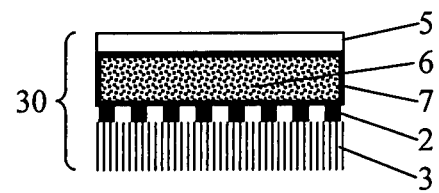
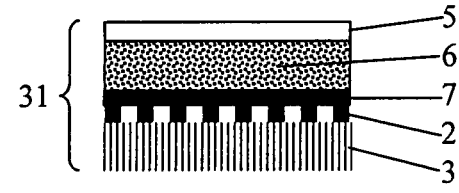
FIG. 1a	FIG. 1b

TRANSDERMAL, THERAPEUTIC SYSTEM WITH ACTIVATABLE OVERSATURATION AND CONTROLLED PERMEATION PROMOTION

CROSS-REFERENCE TO RELATED APPLICATIONS

This application is a National Stage application of International Application No. PCT/EP2005/013133, filed on Dec. 8, 2005, which claims priority of German application number 10 2004 062 614.6, filed on Dec. 24, 2004.

BACKGROUND OF THE INVENTION

1. Field of the Invention

The present invention relates to a transdermal therapeutic system (TTS) that is essentially composed of two compartments and that is provided with activatable oversaturation and controlled permeation promotion. The invention more particularly relates to a TTS wherein an oversaturated active substance solution is produced in an active-substance-containing polymer matrix when the system is applied to the skin, caused by the controlled supply of one or more substances promoting the permeation of the pharmaceutical active substance (permeation enhancers). The present invention further relates to the two compartments that are assembled to form the transdermal therapeutic system according to the invention and to the production of said transdermal therapeutic system from said two compartments.

2. Description of the Prior Art

In practice, it is often difficult to realise the permeation of medicinal active substances through the skin into the blood circulation with the aim of attaining physiologically or therapeutically effective plasma levels or systemic pharmacodynamic effects. The reason for this lies in the skin as such, which, due to its structure and function, constitutes an effective permeation barrier for transdermally applied substances. In order to nevertheless achieve permeation rates with which physiologically or therapeutically active plasma levels can be achieved, the following three methods are predominantly used in practice:

1. addition of substances promoting the permeation of the active substance, so-called permeation enhancers;
2. application of electric current (iontophoresis) and/or ultrasound (phonophoresis); and
3. the use of release systems wherein the active substance is present at a concentration that exceeds its solubility limit in the corresponding vehicles (oversaturated systems).

Other possibilities of improving the transdermal administration of an active substance, such as the use of so-called prodrugs, whose physicochemical properties are more favourable for skin permeation (inter alia, higher lipophilicity), play only a minor part in the development of transdermal administration systems.

However, the methods most frequently used in practice in order to improve the transdermal permeation of active substances involve considerable drawbacks too.

The essential disadvantage in adding permeation enhancers is that the latter, upon application of the release system, leave the system in an uncontrolled manner and, especially in the initial phase of application, very rapidly since said enhancers are, as a rule, readily volatile organic compounds. This uncontrolled overdosage of permeation enhancers (enhancer dose dumping) frequently causes skin irritation. In addition, incorporation of permeation enhancers in the matrix of transdermal therapeutic systems often leads to stability problems since the active substance may interact with the permeation enhancer.

The particular disadvantage of iontophoresis and phonophoresis lies, above all, in their skin irritation potential since both electric current and ultrasound interfere with the skin's barrier function more strongly than chemical permeation enhancers.

Systems oversaturated with active substance have a disadvantage in that they are only metastable and in that the recrystallization processes taking place in the active-substance-containing matrix may lead to a reduction of the bioavailability of the active substance, as well as to an adverse effect on the adhesive power of the transdermal therapeutic systems.

Satisfactory compromise solutions are known whereby oversaturation of the active substance present in the polymer matrix of a transdermal therapeutic system can be maintained as high as possible, while at the same time maintaining it as stable as required.

SUMMARY OF THE PRESENT INVENTION

The object of the present invention is to provide a stable, oversaturated transdermal therapeutic system in the form of a patch.

This object is achieved by a transdermal therapeutic system wherein oversaturation of a pressure-sensitive adhesive polymer matrix with active substance is produced when the system is applied to the skin, and wherein, simultaneously, permeation enhancers are acting in a controlled manner.

It has, surprisingly, been found that a rapid activation of a transdermal therapeutic system to an oversaturated system that has maximum thermodynamic activity and wherein, simultaneously, a controlled action of at least one permeation enhancer takes place can be achieved by a transdermal therapeutic system that is assembled from two compartments when the system is applied and wherein the active substance is present in a first compartment, the verum compartment, in fully crystallised form, that is, in a solid state of aggregation, within a pressure-sensitive adhesive polymer matrix layer and wherein the permeation enhancer(s) is/are present in a second compartment (enhancer compartment) that is a liquid reservoir system and comprises a membrane controlling the release of the permeation enhancer(s).

BRIEF DESCRIPTION OF THE DRAWINGS

FIG. 1 is a schematic representation of two embodiments of the transdermal therapeutic system according to the invention and of the compartments from which it is assembled.

DETAILED DESCRIPTION OF THE INVENTION

Figure 2:
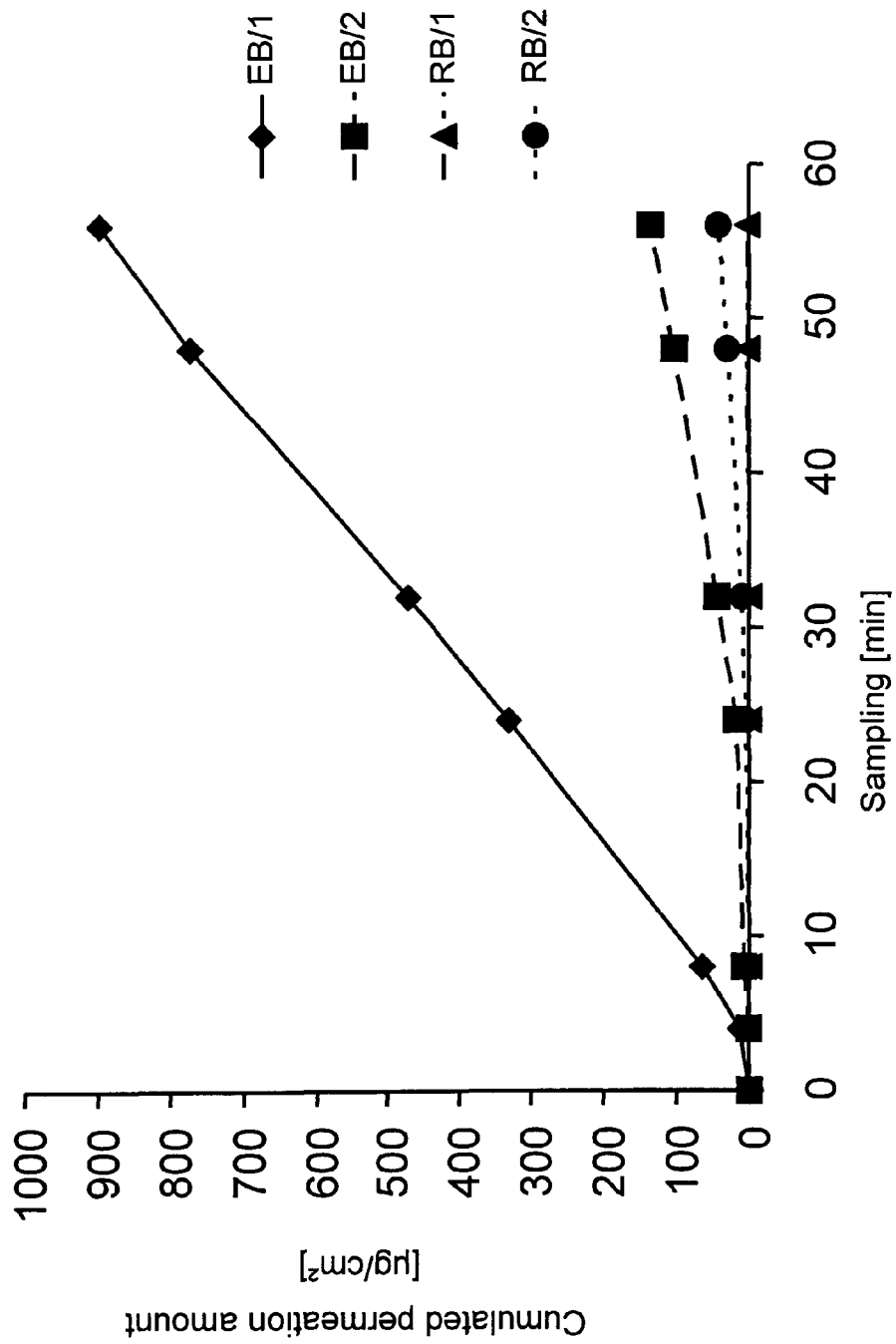
FIG. 2 is a diagram for comparing the permeation profiles of a verum compartment that has been combined with different enhancer compartments, the enhancer compartments differing only with respect to their control membranes.

In the following, the invention will be explained in more detail with reference to the figures and by the examples, but without limiting the invention in any way.

The transdermal therapeutic system (30, 31), as shown in FIGS. 1a and 1b, comprises an active-substance-containing, pressure-sensitive adhesive polymer matrix (3) that is provided, on the side thereof averted from the skin, with a perforated or non-perforated backing layer (2) having a high permeability for the permeation enhancer(s). This perforated or highly permeable backing layer (2) is also called an "inner backing layer". On the side of the inner backing layer (2) that is opposite the polymer matrix (3), the inventive transdermal therapeutic system of the present invention is provided with a liquid reservoir system (6) that comprises a control membrane (7). The covering of the liquid reservoir system (6) itself may, at least on the side facing the verum compartment (discussed below), consist of the control membrane (7) (FIG. 1a), or the control membrane (FIG. 1a) may additionally be applied to the covering of the liquid reservoir system (6) on that side of the system that faces the polymer matrix (3) (FIG. 1b), so that the control membrane (7) is located between the liquid reservoir (6) and the inner backing layer (2). The transdermal therapeutic system (30, 31) additionally comprises a backing layer (5) that is impermeable to the active substance and to the permeation enhancer(s) and that covers the TTS.

The TTS (30, 31) according to the present invention is assembled from the two separately manufactured compartments, a verum compartment (10, 11) and an enhancer compartment (20, 21), when after removal of the detachable, outer backing layer (1) from the verum compartment 10, 11 the system is being applied.

The verum compartment (10, 11) comprises a pressure-sensitive adhesive polymer matrix (3) wherein the active substance is present fully crystallised, that is, in the solid state of aggregation. The pressure-sensitive adhesive polymer matrix (3) is covered on one of its two sides by the inner backing layer (2), which is perforated or has a high permeability for the permeation enhancer(s) contained in the enhancer compartment 20, 21. The inner backing layer (2) is, in turn, covered, on the side thereof that is opposite the pressure-sensitive adhesive polymer matrix (3), by the so-called outer backing layer (1). The outer backing layer (1) is impermeable to active substance and detachable from the inner backing layer (2). The pressure-sensitive adhesive polymer matrix (3) is covered, on the side thereof that is opposite to the inner backing layer (2), by an active-substance-impermeable, detachable backing layer (4).

The pressure-sensitive adhesive matrix layer (3) may consist of pressure-sensitive adhesive polymers based on acrylic acid and/or methacrylic acid as well as the esters thereof, polyacrylates, isobutylenes, ethylene vinyl acetate, natural and/or synthetic rubbers, for example acrylonitrile-butadiene rubber, butyl rubber or neoprene rubber, styrene-diene copolymers such as styrene-butadiene block copolymers or hot-melt adhesives. The matrix layer may also be manufactured on the basis of pressure-sensitive adhesive silicone polymers or polysiloxanes; especially preferred are amine-resistant polydimethyl siloxanes. This list is far from being complete, but reveals the broad applicability of the inventive principle.

For the inner backing layer (2), films may be used by which the permeation enhancer(s), which is/are to be supplied by the enhancer compartment, can diffuse into the active-substance-containing polymer matrix, that is, films that are permeable to the permeation enhancer(s). It is also possible to use films for the inner backing layer (2) that are impermeable to the permeation enhancer(s) and, possibly, also to the active substance and/or further auxiliary substances, provided that these films have been perforated by suitable rolling or punching tools. Preferably, a polyester film is used that has been provided with small holes, the holes preferably having a diameter of 1.0 mm and a commensurate distance from the adjacent holes.

As a material for the outer backing layer (1), such films are suitable as can be detached from the inner backing layer (2) without any difficulty. Suitable are, above all, polyesters, which are characterised by a particular strength. Furthermore, almost any other skin-compatible plastics can be used, such as polyvinyl chloride, ethylene vinyl acetate, vinyl acetate, polyethylene, polypropylene, cellulose derivatives and many others. If required, the film can be rendered detachable by a suitable treatment, e.g. siliconisation, at least of that surface of the film that faces the inner backing layer (2). In individual cases, the film may be provided with an additional overlay, for example by vapour-deposition of metals or with other diffusion-blocking additives, such as silicon dioxide, aluminium oxide or similar substances known to those skilled in the art. Particularly preferred are pressure-sensitive adhesive films based on polyurethane (Opraflex®), polyisobutylene or polyacrylates if the inner backing layer is a film on the basis of polyethylene terephthalate (PET).

The same materials can be used for the detachable protective layer (4) as are used for the outer backing layer (1), provided that they have been rendered detachable by a suitable surface treatment, such as siliconisation. However, other detachable protective layers, such as polytetrafluoroethylene-treated paper, cellophane, polyvinyl chloride or the like, may also be used.

The enhancer compartment (20, 21) is a liquid reservoir system (6), also called bag system, wherein the permeation enhancer(s) is/are present in liquid form, as a gel, a paste or a solution.

The enhancer compartment (20, 21) comprises a control membrane (7) that controls the release of the permeation enhancer(s) from the liquid reservoir system, as well as a backing layer (5) that is impermeable to the permeation enhancer(s) and to the active substance, and a detachable protective film (8) that is likewise impermeable to active substance and to the permeation enhancer(s).

The selection of the permeation enhancer(s) is dependent on their skin-compatibility and on the given active substance. The latter should be soluble, at least partially, in the permeation enhancers or at least in one of the permeation enhancers; of course, it is better if the active substance is highly soluble. Suitable enhancer components that may be used are:
  lower, monohydric alcohols, such as ethanol;
  higher, monohydric alcohols, such as octanol;
  polyhydric alcohols, such as butanediol;
  monosubstituted esters of polyhydric alcohols, such as glycerine monooleate or diethyl glycol monoethyl ether;
  pharmaceutically acceptable terpenes or terpene alcohols, such as limonene or eucalyptol;
  esters of medium-chain carboxylic acids such as diethyl sebacate, methyl laurate or lauryl lactate;
  dimethyl sulfoxide;
  oleic acid;
  dimethyl isosorbide;
  derivatives of polyoxyethylene fatty alcohols, such as Carbowax-350®;
  derivatives of polyoxyethylene fatty alcohol ethers, such as Brij 30®;
  derivatives of polyoxyethylene fatty acid esters, such as Tween 20®;
  partial fatty acid esters of the sorbitans such as Span 20®; and pharmaceutically acceptable liquid $N_2$ compounds such as N-methyl pyrrolidone, diethyl toluamide, dimethylene propylene urea or diethanolamine;

or mixtures of these components with each other.

The control of the release of the permeation enhancer(s) from the enhancer compartment (20, 21) can be achieved through:

the type (chemical composition and pore size) of the control membrane used, and/or the type (chemical composition and layer thickness) of the layer of pressure-sensitive adhesive that is located underneath the control membrane and with which the liquid reservoir system of the enhancer compartment is provided in order to attach the enhancer compartment on the verum compartment, and/or the retarded release through the use of absorption agents in the liquid reservoir system, for example by cyclodextrin or polyvinyl pyrrolidones or cellulose derivatives.

Suitable as the control membrane are thin polymer films of polyethylene (e.g. Solupor®), polypropylene (e.g. Celgard®), polyurethane (e.g. Opraflex®), copolymers of polyethylene and polyvinyl acetate (e.g. EVA®), and silicones (e.g. Silastic®).

The covering of the liquid reservoir system (6) itself may, at least on the side that will later be facing the verum compartment, consist of the control membrane (7) (FIG. 1*a*), or the control membrane may additionally be applied to the covering of the liquid reservoir system (6), namely to that side of the liquid reservoir system (6) that faces the polymer matrix (3), so that the control membrane (7) is arranged between the liquid reservoir (6) and the inner backing layer (2).

Suitable as the pressure-sensitive adhesives having controlling properties are, first of all, such pressure-sensitive adhesives as are based on copolymers of polyethylene and polyvinyl acetate with adhesive resins as additives. Via the ratio of polyethylene to polyvinyl acetate, it is possible to adjust the penetrability or permeability of such a pressure-sensitive adhesive matrix. Also suitable are pressure-sensitive adhesives on the basis of silicones since the latter have a very good diffusibility for most active substances and auxiliary substances.

Apart from the permeation enhancer(s), the liquid reservoir system of the enhancer compartment may also contain viscosity-increasing additives (thickening agents), which do not have a control function. Suitable thickening agents are, for example, finely dispersed silicon oxide such as, for example, Aerosil R 974®, polyacrylic acid such as Carbopol 934P®, mineral oils, wool fats or high-molecular polyethylene glycols such as Carbowax 1000®.

For the detachable protective film (8), the same materials are suitable as are suitable for the detachable protective layer (4) or the outer backing layer (1) of the verum compartment; however, it has to be ensured that the material does not react with the components in the liquid reservoir system, not even with a single one of these components.

At storage conditions, the individual compartments of the TTS according to the present invention are stable and free of unwanted byproducts since there is no oversaturation, and it is therefore impossible for the problem of metastability or a tendency to recrystallise to occur during storage. The recrystallisation processes taking place during the application period of the TTS have no influence on the bioavailability of the active substance, provided that the diffusion rate of the active substance is lower than its rate of release from the crystals or its dissolution rate.

The TTS according to the invention is not produced until the exact time when it is applied, said production being accomplished by sticking the enhancer compartment as an overlying patch onto the verum compartment. Preferably, to this end, after removal of the protective layer of the verum compartment, the latter is initially attached to the skin, and, subsequently, the outer backing layer (1) of the verum compartment (1) is peeled off. After removal of its protective film (8), the enhancer compartment is stuck onto the verum compartment.

Immediately after the application of the enhancer compartment to the verum compartment, the permeation enhancer(s) can diffuse into the verum compartment in a controlled fashion. The first active substance crystals are dissolved immediately after the application of the enhancer compartments, and there is immediately an oversaturated active substance solution, having the highest possible thermodynamic activity, in the matrix. Furthermore, this thermodynamic activity will remain stable for a very long time since the solvent (=permeation enhancer) is delivered to the active substance donor compartment (verum compartment) in a controlled manner.

The present invention thus combines the advantages of liquid reservoir systems and of matrix-controlled TTS systems while at the same time eliminating their disadvantages (e.g. limited active substance and enhancer loading capacities in the case of matrix systems; a high potential for skin irritation, owing to rapid and high release of enhancers, and a risk of dose dumping in the case of liquid reservoir systems).

EXAMPLE 1

Manufacture of a Verum Compartment 54 g of an EVA copolymer, with 40%-wt. vinyl acetate and a melt index of 55 (EVATANE 40/55®), is introduced in 80 g of a solvent mixture, consisting of 2 parts special boiling point gasoline of type 80/110 and 1 part propyl acetate, and stirred at 50° C., with addition of heat. After stirring for about 30 min, a viscous, colourless to slightly cloudy solution was obtained. Subsequently, 66 g of the adhesive resin Foral® 85 E was introduced and stirred until it had been dissolved completely (approx. 15 min), likewise at 50° C. This resulted in a 45.7%, low-viscous, yellowish and slightly cloudy solution (adhesive solution A) that, even after having cooled down, was still present as a stirrable adhesive solution.

To prepare the self-adhesive, active-substance-containing matrix, 8.75 g of adhesive solution A was provided, into which 1.0 g moxonidine base, a lipophile, hardly water-soluble medicinal active substance, was introduced in portions while stirring. This preparation was then homogenised for a total of 30 minutes at a stirring speed of 350 rpm. This was followed by degasification for 15 minutes at 45° C. in an ultrasound bath in order to remove excess air from the material.

The active-substance-containing adhesive material was then spread onto a siliconised polyethylene terephthalate film, using a doctor knife, in a wet layer thickness of 300 µm. Then, the solvents were removed by drying for 30 minutes at 50° C. in a drying cupboard, with drawing-off air duct.

Subsequently, the solvent-free, active-substance-containing adhesive film was covered with a 15-µm-thick, active-substance-impermeable and auxiliary-substance-impermeable polyester film by laminating, said polyester film having previously been perforated by an appropriate rolling or punching tool such that both the size of the holes and the distance between the holes, in all directions, was 1.0 mm.

For the purpose of storing the verum compartment, the perforated cover layer (inner backing layer) was laminated, in addition, with a 15-μm-thick, active-substance-impermeable and auxiliary-substance-impermeable film of polyester (outer backing layer), which, for reversible attachment on the inner backing layer, was coated on one of its sides with a pressure-sensitive adhesive layer of polyisobutylene (Oppanol® B10/B100).

After the manufacture was completed, the active substance portion contained in the pressure-sensitive adhesive matrix was 20%-wt.; the active substance was present in the verum compartment in fully crystallised form.

EXAMPLE 2

Preparation of Enhancer Compartments Comprising a Self-Adhesive Control Membrane To prepare the self-adhesive enhancer compartment (liquid reservoir system), first, the active-substance-free adhesive solution A (Example 1) was spread onto a siliconised polyethylene terephthalate film at a wet-layer thickness of 300 μm by using a doctor knife. Then, the solvents were removed by drying for 30 minutes at 50° C. in a drying cupboard with a drawing-off air duct. The solvent-free and active-substance-free adhesive film was then covered with a 35-μm-thick polyurethane film (Opraflex®, from the company of Lohmann, Germany) (embodiment according to the invention EB1) or with a 25-μm-thick polypropylene film (Celgard X-20®, Celanese Separation Products, USA) by laminating. These films will eventually form the control membranes. Thereafter, a polyester film (Scotchpak No. 1220®, from the company of 3M, Germany) was placed on this Opraflex® or Celgard® film, and bags were made by using a special sealing mask, heated by a commercial electric iron, the bags having a round reservoir of a diameter of 25 mm.

The respective enhancer mixture was filled into the reservoir via an existent opening in the sealed margin of the bags by using a syringe. After filling, the filling aperture was fused using the electric iron, so that an entirely closed and storage-stable liquid reservoir system was obtained.

EXAMPLE 3

Permeation Profiles of TTS

To be able to examine the permeation properties of TTS's according to the invention and to compare these properties with one another, permeation measurements were performed on the in-vitro diffusion model of human full-thickness skin by using modified Franz diffusion cells. The experimental results are graphically represented in FIG. 2.

The acceptor medium used was physiological sodium chloride solution with an addition of 0.1% of $NaN_3$ as a preservative, thermostatted to 32° C.

Used as the enhancer mixture in the reservoir of the enhancer compartment was 300 mg of a mixture of ethanol:oleic acid:N-methyl pyrrolidone with a ratio of 2:1.5:1.5 (v/v/v).

For the embodiment EB/1 of a TTS according to the present invention, the enhancer compartment EB1 according to Example 2 was, after removal of the siliconised polyethylene terephthalate film, attached as an overlying patch on a verum compartment according to Example 1.

As an alternative embodiment EB/2 of a TTS according to the present invention, the enhancer compartment EB2 according to Example 2 was used as an overlying patch instead of the enhancer compartment EB1.

As Reference RB/1, a verum compartment according to Example 1 was used, wherein the 15-μm-thick, active-substance-impermeable and auxiliary-impermeable polyester film, which had been laminated to the matrix, had not been perforated and, in addition, did not comprise a further, outer backing layer and was used in the experiments without an overlying enhancer patch.

As a further reference (RB/2), a conventional matrix-controlled TTS with enhancer was used.

FIG. 2 illustrates the permeation of the active substance for the inventive embodiments EB/1 and EB/2, which is higher than that of Reference Examples RB/1 and RB/2.

EXAMPLE 4

Influence of the Control Membrane on the Permeation of Enhancers

To examine the influence of the control membrane on the permeation of enhancers, permeation measurements were performed on the in-vitro diffusion model of polyurethane membrane by using modified Franz diffusion cells wherein a non-adhesive polyurethane membrane (Opraflex®, from the company of Lohmann, Del.) was used as the diffusion membrane. The acceptor medium used in all of the cases was physiological sodium chloride solution with an addition of 0.1% of $NaN_3$ as preservative, thermostatted to 32° C.

As an enhancer mixture, 300 μl of ethanol:oleic acid:N-methyl pyrrolidone at a ratio of 2:1.5:1.5 (v/v/v) was applied, in each case, to the membrane located on the diffusion membrane.

Figure 3A:
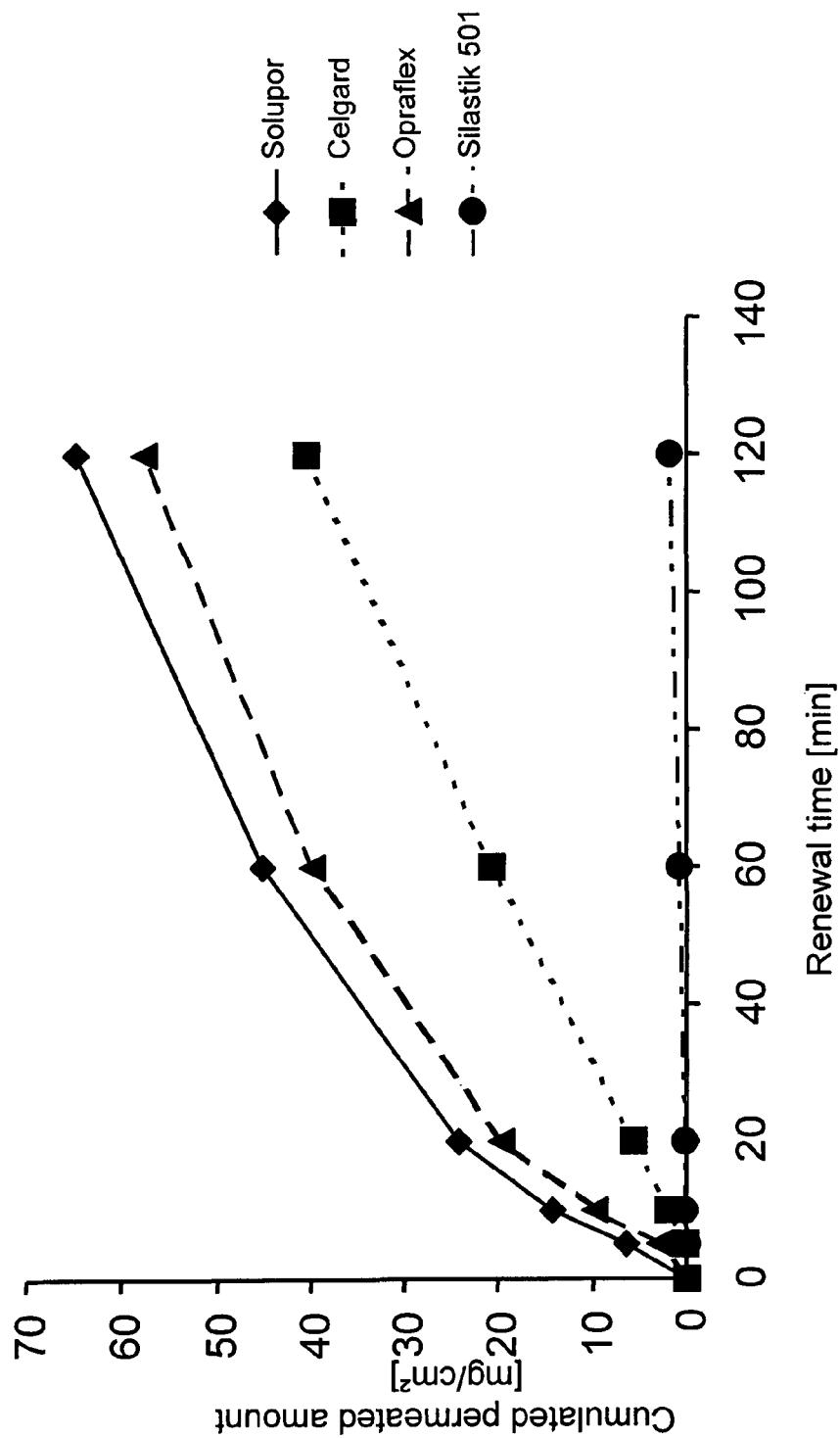
FIG. 3 comprises two diagrams illustrating the results of experiments on the selection of membranes for controlling the permeation of an enhancer.
Figure 3B:
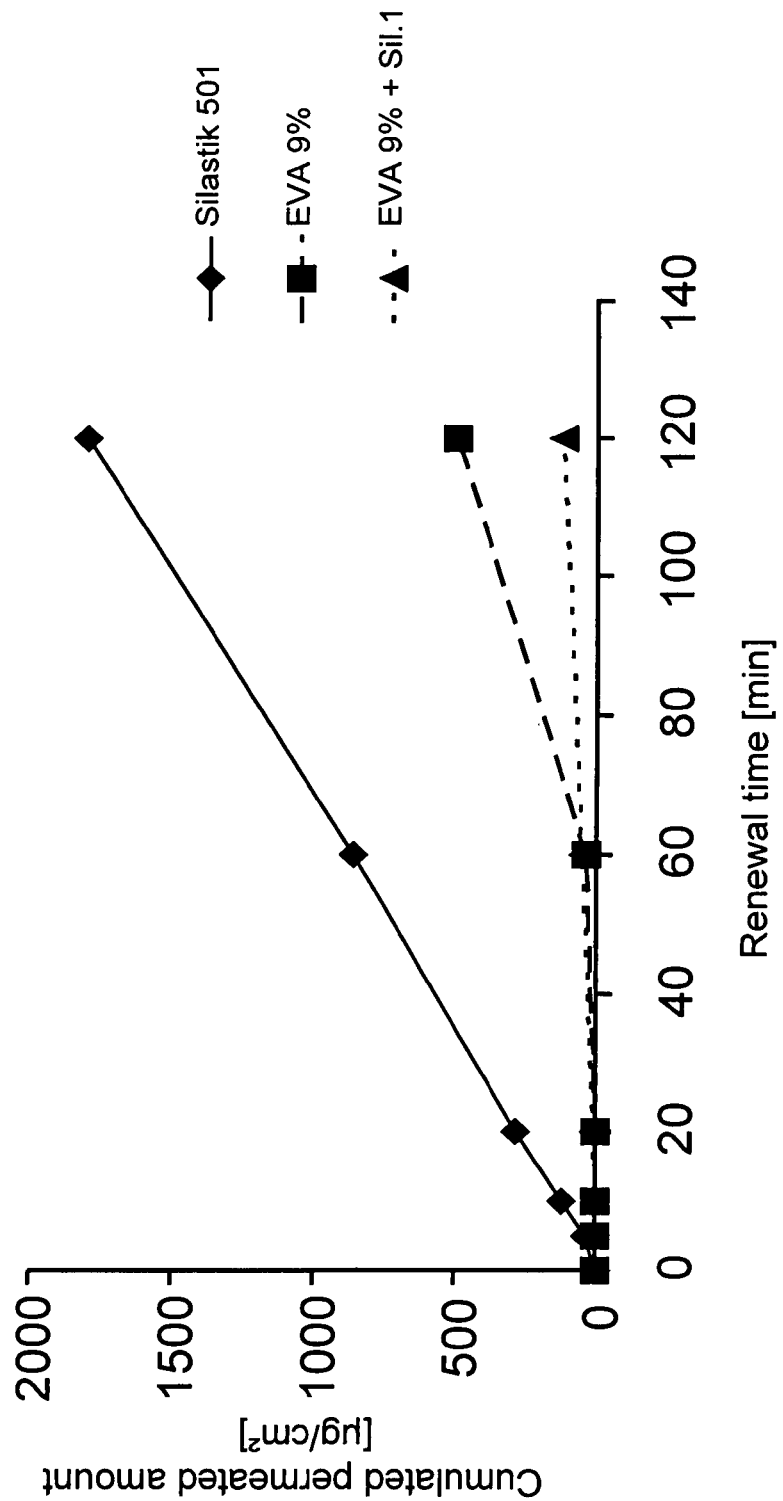

The membranes used as the control membrane can be seen from the legends to the diagrams of FIGS. 3a and 3b. All of the control membranes were provided with a 300-μm-thick coating of pressure-sensitive adhesive based on copolymers of polyethylene and polyvinyl acetate (adhesive solution A according to Example 1), by which they were attached to the diffusion membrane. The diagrams in FIGS. 3a and 3b illustrate the permeation of N-methyl pyrrolidone against the chosen control membrane.

EXAMPLE 5

Influence of the Absorption Agent Present in the Liquid Reservoir of the Enhancer Compartment on the Controlled Enhancer Permeation, as Measured on the Enhancer Example N-Methyl Pyrrolidone Permeation measurements were performed on the in-vitro diffusion model of polyurethane membrane by using modified Franz diffusion cells, wherein a non-adhesive polyurethane membrane (Opraflex®, from the company of Lohmann, Del.) was used as the diffusion membrane. The acceptor medium used was physiological sodium chloride solution with an addition of 0.1% of $NaN_3$ as preservative, thermostatted to 32° C.

Figure 4:
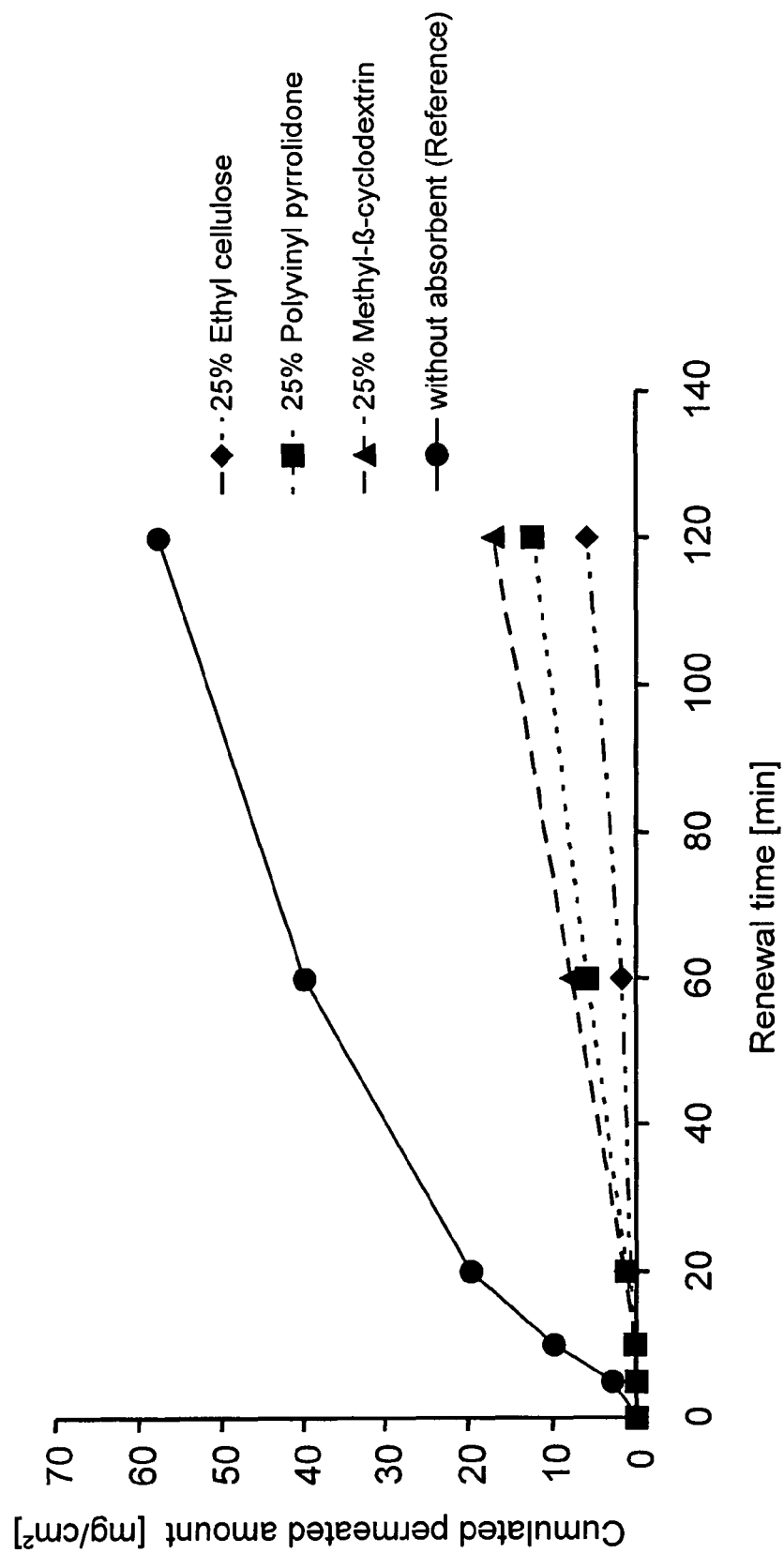
FIG. 4 is a diagram illustrating the effect of absorbents in the liquid reservoir of an enhancer compartment.

As an enhancer mixture, 800 mg of ethanol:oleic acid:N-methyl pyrrolidone 2:1.5:1.5 (v/v/v), mixed with the absorption agents as included in the legend to FIG. 4, was applied directly to the control membrane (Celgard® with pressure-sensitive adhesive layer).

The diagram of FIG. 4 illustrates the influence of various absorption agents on the permeation of N-methyl pyrrolidone.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

I claim:

1. A transdermal therapeutic system (TTS), comprising a first compartment and a second compartment, wherein said first compartment comprises a detachable, outer backing layer and a pressure-sensitive adhesive polymer matrix containing an active substance in a solid state of aggregation, wherein one side of said pressure-sensitive adhesive polymer matrix fixes said transdermal therapeutic system on the skin, and comprises an active substance-impermeable, detachable protective layer for covering the side of said pressure-sensitive adhesive polymer matrix for fixing said transdermal therapeutic system on the skin; and wherein said second compartment is an enhancer compartment comprising a liquid zreservoir system containing at least one skin permeation enhancer in liquid form, wherein said active substance is at least partially soluble in said at least one skin permeation enhancer;

and wherein said first compartment and said second compartment, in the condition of manufacture, are present separate from each other and are connectable with each other after removal of the detachable, outer backing layer from the first compartment for applying said first compartment and said second compartment in such a way that the side of the first, active substance-containing compartment which is opposite the side covered with the detachable protective layer is connected with the second, enhancer-containing compartment, wherein the second enhancer-containing compartment further comprises a control membrane for controlling diffusion of the at least one skin permeation enhancer into the active substance-containing compartment for forming an oversaturated system of the active substance;

and wherein said transdermal therapeutic system further comprises an inner backing layer for separating said first compartment and the enhancer compartment, after having been combined with one another, wherein said inner backing layer is perforated or is a layer having high permeability to said at least one skin permeation enhancer.

2. The transdermal therapeutic system according to claim 1, wherein said at least one skin permeation enhancer is contained in the liquid reservoir system of the enhancer compartment in a solution.

3. The transdermal therapeutic system according to claim 1, wherein said at least one skin permeation enhancer from the enhancer compartment is selected from the group consisting of alcohols, monosubstituted esters of polyhydric alcohols, terpenes, terpene alcohols, esters of medium-chain carboxylic acids, polyoxyethylene fatty alcohols, polyoxyethylene fatty alcohol ethers, polyoxyethylene fatty acid esters, partial fatty acid esters of the sorbitans, dimethyl isosorbide, dimethyl sulfoxide, oleic acid, and pharmaceutically acceptable liquid nitrogen compounds.

4. The transdermal therapeutic system according to claim 3, wherein alcohols are selected from the group of alcohols consisting of lower monohydric alcohols, higher monohydric alcohols, and polyhydric alcohols, and wherein said pharmaceutically acceptable liquid nitrogen compounds are selected from the group consisting of N-methyl pyrrolidone, diethyl toluamide, dimethylene propylene urea and diethanolamine.

5. The transdermal therapeutic system according to claim 1, wherein said control membrane is applied to the side of the liquid reservoir system that faces the first compartment when combined with the second compartment.

6. The transdermal therapeutic system according to claim 1, wherein said control membrane is self-adhesive or comprises a pressure-sensitive adhesive layer for combining the first and second compartments.

7. The transdermal therapeutic system according to claim 1, wherein said control membrane is selected from the group of polymer films consisting of polyethylenes, polypropylenes, silicones, polyurethanes, and copolymers of polyethylene and polyvinyl acetate.

8. The transdermal therapeutic system according to claim 6, wherein said pressure-sensitive adhesive layer of the control membrane comprises polymers selected from the group consisting of silicones and copolymers of polyethylene and polyvinyl acetate.

9. The transdermal therapeutic system according to claim 6, wherein the controlled diffusion of the at least one skin permeation enhancer is dependent on the layer thickness of said pressure-sensitive adhesive layer of the control membrane.

10. The transdermal therapeutic system according to claim 7, wherein the pressure-sensitive adhesive layer of the control membrane comprises copolymers of polyethylene and polyvinyl acetate and a permeability of said pressure-sensitive adhesive layer of the control membrane is adjusted via the ratio of polyethylene to polyvinyl acetate.

11. The transdermal therapeutic system according to 1, wherein said liquid reservoir system of the second compartment further comprises at least one absorption agent selected from the group consisting of cyclodextrins, polyvinyl pyrrolidones and cellulose derivatives.

12. The transdermal therapeutic system according to claim 1, wherein said liquid reservoir system of the second compartment further comprises auxiliary substances in the sense of thickening agents selected from the group consisting of mineral oils, wool fats, polyacrylic acid, high-molecular polyethylene glycols and finely dispersed silicon dioxide.

13. The transdermal therapeutic system according to claim 1, wherein said pressure-sensitive adhesive polymer matrix in the first compartment comprises polymers based on at least one selected from the group consisting of acrylic acid, methacrylic acid, esters of acrylic acid and methacrylic acid, polyacrylates, isobutylenes, ethylene vinyl acetate, natural rubbers, synthetic rubbers, styrene-diene copolymers and hot-melt adhesives, silicone polymers and polysiloxanes.

14. The transdermal therapeutic system according to claim 13, wherein said synthetic rubbers are selected from the group consisting of acrylonitrile-butadiene rubber, butyl rubber and neoprene rubber, said styrene-diene copolymers are styrene-butadiene block copolymers and wherein said polysiloxanes are amine-resistant polydimethyl siloxanes.

15. The transdermal therapeutic system according to claim 1, wherein said inner backing layer is a polyester film provided with holes.

16. The transdermal therapeutic system according to claim 1, wherein said inner backing layer is a polyester film provided with holes or said inner backing layer is a film based on polyethylene terephthalate.

17. The transdermal therapeutic system according to claim 1, wherein a material for said detachable, outer backing layer and for the detachable protective layer is selected from the group consisting of polyesters, polyvinyl chloride, ethylene vinyl acetate, vinyl acetate, polyethylene, polypropylene and cellulose derivatives.

18. The transdermal therapeutic system according to claim 1, wherein a surface treatment renders at least one of said detachable, outer backing layer and said detachable protective layer detachable.

19. The transdermal therapeutic system according to claim 18, wherein said surface treatment is siliconisation.

20. The transdermal therapeutic system according to claim 1, wherein said detachable, outer backing layer comprises an additional overlay.

21. The transdermal therapeutic system according to claim 20, wherein said additional overlay is a vapour deposition of metals or other diffusion-blocking additives.

22. The transdermal therapeutic system according to claim 21, wherein said other diffusion-blocking additives are selected from the group consisting of silicon dioxide and aluminium dioxide.

23. The transdermal therapeutic system according to claim 1, wherein said detachable protective layer is selected from the group consisting of polytetrafluoroethylene-treated paper, cellophane and polyvinyl chloride.

24. The transdermal therapeutic system according to claim 1, wherein said enhancer compartment comprises a bag-shaped liquid reservoir system wherein at least one skin permeation enhancer is contained in a solution, and further comprises a backing layer impermeable to active substance and to permeation enhancers.

25. The transdermal therapeutic system according to claim 24, wherein said at least one permeation enhancer is selected from the group consisting of alcohols, monosubstituted esters of polyhydric alcohols, terpenes, terpene alcohols, esters of medium-chain carboxylic acids, polyoxyethylene fatty alcohols, polyoxyethylene fatty alcohol ethers, polyoxyethylene fatty acid esters, partial fatty acid esters of the sorbitans, dimethyl isosorbide, dimethyl sulfoxide, oleic acid, and pharmaceutically acceptable, liquid nitrogen compounds.

26. The enhancer compartment according to claim 25, wherein said alcohols are selected from the group consisting of lower monohydric alcohols, higher monohydric alcohols, and polyhydric alcohols, and said pharmaceutically acceptable, liquid nitrogen compounds are selected from the group consisting of N-methyl pyrrolidone, diethyl toluamide, dimethylene propylene urea and diethanolamine.

27. The transdermal therapeutic system according to claim 24, wherein said control membrane is applied to the side of the liquid reservoir system that faces the first compartment when combined with the second compartment.

28. The transdermal therapeutic system according to claim 24, wherein said control membrane is self-adhesive or comprises a pressure-sensitive adhesive layer for combining said first and second compartments.

29. The transdermal therapeutic system according to claim 24, wherein said control membrane is selected from the group of polymer films consisting of polyethylenes, polypropylenes, silicones, polyurethanes, and copolymers of polyethylene and polyvinyl acetate.

30. The transdermal therapeutic system according to claim 28, wherein said pressure-sensitive adhesive layer of the control membrane comprises polymers selected from the group consisting of silicones and copolymers of polyethylene and polyvinyl acetate.

31. The transdermal therapeutic system according to claim 30, wherein the pressure-sensitive adhesive layer of the control membrane comprises copolymers of polyethylene and polyvinyl acetate and a permeability of said pressure-sensitive adhesive layer of the control membrane is adjusted via the ratio of polyethylene to polyvinyl acetate.

32. The transdermal therapeutic system according to claim 24, wherein said liquid reservoir system of the second compartment additionally comprises at least one absorption agent that is selected from the group consisting of cyclodextrins, polyvinyl pyrrolidones and cellulose derivatives.

33. The transdermal therapeutic system according to claim 24, wherein said liquid reservoir system of the second compartment comprises additional auxiliary substances in the sense of thickening agents selected from the group consisting of mineral oils, wool fats, polyacrylic acid, high-molecular polyethylene glycols and finely dispersed silicon dioxide.

34. The transdermal therapeutic system according to claim 28, wherein said enhancer compartment further comprises a detachable protective film.

\* \* \* \* \*